United States Patent

Sawyer

[11] Patent Number: 5,872,269
[45] Date of Patent: Feb. 16, 1999

[54] ESTERIFICATION PROCESS HEAT RECOVERY

[75] Inventor: Gary A. Sawyer, Media, Pa.

[73] Assignee: Arco Chemical Technology, L.P., Greenville, Del.

[21] Appl. No.: 74,680

[22] Filed: May 8, 1998

[51] Int. Cl.[6] .......................... C07C 51/00; C07C 51/363
[52] U.S. Cl. .......................... 554/169; 554/149; 554/167; 554/168
[58] Field of Search .................................. 554/169, 149, 554/168, 167

[56] References Cited

U.S. PATENT DOCUMENTS

| | | |
|---|---|---|
| 4,861,613 | 8/1989 | White et al. . |
| 4,983,329 | 1/1991 | Cooper . |
| 5,110,508 | 5/1992 | Buttegen et al. ........................ 554/170 |
| 5,466,843 | 11/1995 | Cooper .................................... 554/149 |
| 5,571,935 | 11/1996 | Sekula et al. . |
| 5,681,939 | 10/1997 | Ferenz . |

FOREIGN PATENT DOCUMENTS 59-240737  11/1984  Japan .

*Primary Examiner*—Paul J. Killos
*Assistant Examiner*—Jafar Parsa
*Attorney, Agent, or Firm*—William C. Long

[57] ABSTRACT

Economics of heat are achieved in a process for batch fatty acid esterification of alkoxylated polyol by transferring the reaction mixture to a holding vessel and subsequently heating fresh feed to the batch reaction by indirect heat exchange with the transferred reaction mixture.

3 Claims, 1 Drawing Sheet

ESTERIFICATION PROCESS HEAT RECOVERY

BACKGROUND OF THE INVENTION

1. Field of the Invention

The present invention relates to the esterification of alkoxylated polyols and especially to the efficient recovery of heat in the esterification process.

2. Description of the Prior Art

The preparation of esters of alkoxylated polyols is known. A particularly important technology relates to the preparation of food grade quality esters of propoxylated glycerin as described, for example, in U.S. Pat. Nos. 4,983,329, 5,571,925, 5,681,939, and the like. Generally, the alkoxylated polyol esterification is carried out at elevated temperatures, and effective and efficient recovery of heat is an important process consideration.

The present invention provides such a process having efficient and improved heat recovery.

BRIEF DESCRIPTION OF THE INVENTION

In accordance with the present invention, alkoxylated polyol is esterified in a batch reaction system; an essential feature of the present invention is the provision of a holding tank separate from the esterification reactor to which the reaction mixture is transferred at the completion of the esterification reaction. The transferred reaction mixture is then cooled by indirect heat exchange with fresh reactants being charged to the batch reactor thus effectively minimizing external heat requirements while bringing the reactants to reaction temperature.

DETAILED DESCRIPTION

Figure 1:
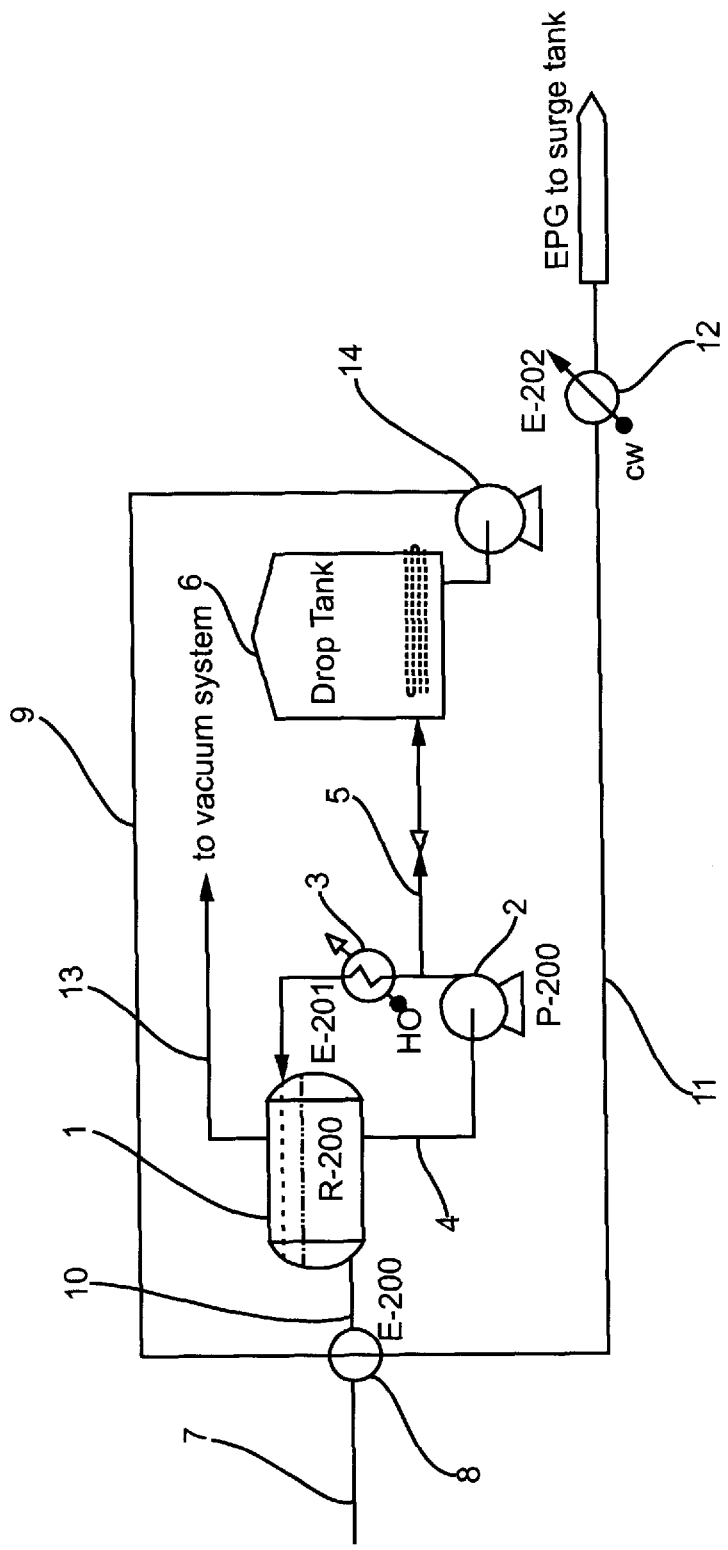
FIG. 1 illustrates schematically an embodiment of the invention.

Referring to the attached drawing reactor 1 is a stirred batch reactor suitable for carrying out the esterification of alkoxylated polyol at elevated temperature. The reaction system is equipped with pump 2 and heat exchanger 3 in order to control temperature during the batch reaction. Reaction liquid is removed from reactor 1 via line 4 and is pumped through exchanger 3 where temperature is regulated as required. After completion of a batch esterification, the reaction mixture, at elevated temperature, is transferred via lines 4 and 5 to holding tank 6 which has sufficient capacity to hold the entire reaction mixture from reactor 1 and which preferably is insulated to prevent heat loss.

When reactor 1 is ready to receive a fresh charge of reactants for the start of a new batch reaction, the fresh reactants are transferred via line 7 to heat exchanger 8 wherein the fresh reactants are heated by indirect heat exchange with the hot reaction mixture carried from holding tank 6 via line 9. In exchanger 8, the fresh reactants are heated by the indirect heat exchange and pass via line 10 from the exchanger to reactor 1 while the reaction mixture which is transferred from tank 6 via pump 14 and line 9 to exchanger 8 and therein is cooled by the indirect heat exchange and passes from exchanger 8 via line 11 to product separation (not shown). If required, supplemental heating means (not shown) can be provided to further heat the fresh reactants fed to reactor 1; exchanger 12 can be provided to further cool the reaction mixture.

The present invention is especially applicable to the preparation of fatty acid-esterified propoxylated glycerins which have been proposed for use as reduced calorie fat substitutes in food products as disclosed, for example, in U.S. Pat. No. 4,861,613.

The propoxylated glycerin reactant employed may be prepared by any of the standard methods known in the art such as, for example, the base catalyzed reaction of propylene oxide with glycerin. While the molar ratio of propylene oxide to glycerin is not critical, if the esterified propoxylated glycerin is to be used as a reduced calorie fat substitute, it is preferred that from 2 to 20 moles of epoxide be reacted per mole of glycerin. The propoxylation of glycerin can be carried out by the addition of propylene oxide to glycerin in the presence of a catalytic amount of an alkali metal alkoxylate at a temperature of from about 70° C. to 130° C. The alkali metal alkoxylate is desirably prepared by heating an alkali metal compound such as sodium hydroxide or potassium hydroxide with glycerin at an elevated temperature while continuously removing water preferably under reduced pressure. Preferably sufficient catalyst is present during propoxylation to provide an alkali metal content of about 0.0003 moles to 3.3 moles alkali metal per 100 g of glycerin. The propylene oxide can be fed incrementally into a reactor containing the glycerin and catalyst at a rate sufficient to maintain a pressure within the reactor of about 40 to 80 psia. The degree of propoxylation is controlled, and thus the molecular weight of the propoxylated glycerin as well, by regulating the amount of propylene oxide fed to the reactor. After the desired molecular weight is reached the alkali metal may be removed prior to esterification by any suitable method such as adsorption, ion exchange, or extraction.

The propoxylated glycerin thus obtained will have a chemical structure generally as follows:

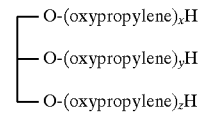

wherein x, y, and z are the same of different and are 0 or preferably an integer of from 1 to 20 with the sum of $x+y+z$ preferably ranging from 2 to 20 (more preferably, 3 to 15). The oxypropylene units in the propoxylated glycerin have the structure

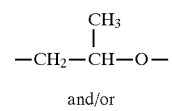

and/or

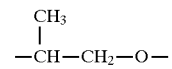

with the former type of structure preferably predominating.

The fatty acids which may be employed as reactants may be saturated or unsaturated fatty acids or mixtures thereof. Straight chain as well as branched fatty acids may be used. Preferably, the fatty acid is a $C_{10}$–$C_{24}$ fatty acid (i.e., an acid which contains from 10 to 24 carbon atoms). An excess of fatty acid, preferably from 1 to 40% molar excess relative to the amount of propoxylated glycerin, is employed in the present process in order to catalyze the desired esterification such that the desired esterified propoxylated glycerin product may be rapidly obtained without adding other catalysts.

Illustrative of the $C_{10}$–$C_{24}$ fatty acids which may be utilized are saturated acids such as capric, lauric, myristic, pentadecanoic, palmitic, heptadecanoic, stearic, nonadecanoic, eicosanoic, and behenic acid. Unsaturated fatty acids which are suitable for use include palmitoleic, oleic, linoleic, linolenic, and arachidonic acid. The mixtures of fatty acids which are conveniently available by conventional splitting (hydrolysis) of natural and hydrogenated vegetable oils and animal fats are also appropriate for use such as, for example, soybean oil fatty acids, hydrogenated vegetable oils and animal fats are also appropriate for use such as, for example, soybean oil fatty acids, hydrogenated high erucic rapeseed oil fatty acids, coconut oil fatty acids and the like. The process may be advantageously performed with 5–25% molar excess fatty acid.

The propoxylated glycerin and the fatty acid are preheated as described above in exchanger 8 and introduced into reactor 1 wherein the esterification takes place in accordance with known procedures. While the configuration and design of the reaction zone is not critical, a reactor vessel should be selected which is capable of heating and agitating (mixing) the contents for the vessel. Means for introducing the reactants and for removing the water of reaction (preferably, as an overhead stream in vapor form via line 13) from the vessel should also be provided. It may be advantageous to utilize equipment which will provide high shear mixing (e.g. a 5 to 600 m/min. tip speed which typically may be achieved by a drive motor energy input of 1.5 to 3 kilowatts per 1000 liters of reaction mixture). Thin film reaction systems may also be employed. In a particularly desirable embodiment of the invention, no materials other than the fatty acid and the propoxylated glycerin are introduced into the reaction zone; i.e., no catalyst, solvent, entrainer, or azeotropic stripping agent is present.

Generally, the esterification is carried out at temperatures of 100° C. to about 250° C., preferably 180° C. to 250° C. Reaction times are illustratively 4 to 15 hours. Once the desired degree of esterification has been achieved, the reaction product mixture is transferred to holding tank 6 and thence to exchanger 8 before being removed via line 11. Residual unreacted fatty acid should be removed from the esterified propoxylated glycerin so as to lower the acidity to a level which will be acceptable in food applications. Suitable methods include vacuum steam stripping (distillation) at an elevated temperature (as described, for example, in U.S. Pat. No. 4,983,329), alkali neutralization to precipitate fatty acid salts which may then be removed by filtration, extraction (with methanol, for example) and dilution with a solvent such as hexane in which the desired product is soluble and the fatty acid is insoluble and the precipitated fatty acid removed by filtration.

The esterified propoxylated glycerin can be additionally purified or treated so as to render it more suitable for use in food compositions using any of the techniques known in the art for refining natural vegetable or animal oils and fats. Such techniques include, but are not limited to, degumming, bleaching, filtration, deodorization, hydrogenation, dewaxing and the like. Various additives such as stabilizers, anti-oxidants, vitamins and so forth can also be incorporated into the esterified propoxylated glycerin.

Practice of the invention reduces utility costs, reduces furnace size, reactor size and cycle time thus substantially improving process economics.

The following example illustrates the invention:

At the completion of a batch reaction, reactor 1 contains 286,078 lbs of a mixture which is comprised of 15 wt % unreacted fatty acid, 1200 ppm of the monoester of the propoxylated glycerin, 8.5 wt % of the diester of propoxylated glycerin and the balance the triester of propoxylated glycerin. The reaction mixture is at a temperature of 240° C. The reaction mixture is transferred over 55 minutes via lines 4 and 5 to holding tank 6. A new reactor charge comprising a simultaneous flow of 120,084 lbs of hydrogenated fatty acids from soya bean oil, 98,250 lbs of hydrogenated fatty acids from rapeseed oil, and 78,643 lbs propoxylated glycerin is charged via line 7 through exchanger 8 and line 10 to reactor 1 over a 190 minute period. Simultaneously the contents of holding task 6 are passed through exchanger 8 via line 9 wherein heat is transferred by indirect exchange between the reaction mixture from tank 6 and the new feed being charged via line 7. The feed to the reactor is heated to 221° C. and the reaction mixture cooled to 109° C. by this exchange. After the transfer is complete the contents of reactor 1 are heated to 240° C. reaction temperature and held there for 235 minutes to complete the new batch reaction.

Use of this invention reduces heat consumption from 250 Btu/lb product to 58 Btu/lb product, and shortens the cycle time by 229 minutes. Despite the addition of the holding tank, pumps and exchanger the installed capital cost is reduced by $0.6 million because of a smaller reactor and smaller furnaces to generate steam and hot oil.

I claim:

1. In a batch process for the fatty acid esterification of alkoxylated polyol, the improvement wherein the reaction product mixture from a first esterification reaction is passed from the esterification reactor to a holding tank and thereafter is passed from the holding tank to a heat exchanger wherein by indirect heat exchange the said reaction product mixture transfers heat to fresh reactants being fed to batch reaction in said esterification reactor.

2. The process of claim 1 wherein the alkoxylated polyol is propoxylated glycerin.

3. The process of claim 1 wherein the fatty acid is a $C_{10}$–$C_{24}$ fatty acid.

* * * * *